United States Patent [19]

Appel et al.

[11] Patent Number: 5,488,177
[45] Date of Patent: Jan. 30, 1996

[54] METHOD FOR THE PREPARATION OF ALKYL HYDROPEROXIDE SOLUTIONS CONTAINING LITTLE OR NO WATER

[75] Inventors: Hans Appel, Hollriegelskreuth; Fritz Diem, Munich, both of Germany

[73] Assignee: Peroxid-Chemie GmbH, Hollriegelskreuth, Germany

[21] Appl. No.: 331,593

[22] PCT Filed: Sep. 27, 1993

[86] PCT No.: PCT/EP93/02620

§ 371 Date: Nov. 1, 1994

§ 102(e) Date: Nov. 1, 1994

[87] PCT Pub. No.: WO94/07854

PCT Pub. Date: Apr. 14, 1994

[30] Foreign Application Priority Data

Sep. 28, 1992 [DE] Germany .................. 42 32 500.5

[51] Int. Cl.⁶ ............................................. C07C 409/00
[52] U.S. Cl. ............................................................ 568/576
[58] Field of Search ................................................. 568/576

[56] References Cited

U.S. PATENT DOCUMENTS

| 4,891,101 | 1/1990 | Sullivan | 203/36 |
| 5,104,493 | 4/1992 | Chong | 203/91 |

FOREIGN PATENT DOCUMENTS

| 135295 | 3/1985 | European Pat. Off. . |
| 6099430 | 8/1981 | Japan . |
| 3066660 | 3/1991 | Japan . |
| 3190856 | 8/1991 | Japan . |
| 1137717 | 12/1968 | United Kingdom . |
| 1232710 | 5/1971 | United Kingdom . |

*Primary Examiner*—Paul J. Killos
*Attorney, Agent, or Firm*—Felfe & Lynch

[57] ABSTRACT

A method is described for the preparation of solutions containing little or no water of tertiary alkyl hydroperoxides in inert solvents by dewatering with sulfuric acid, according to which one or more inert organic solvents are added to an aqueous solution as well as sulfuric acid in such amount and concentration that in the aqueous phase forming after the mixing followed by separation of the phases there is at least 49% of $H_2SO_4$ and the water content in the organic phase amounts to no more than 2.5%.

23 Claims, No Drawings

1

METHOD FOR THE PREPARATION OF ALKYL HYDROPEROXIDE SOLUTIONS CONTAINING LITTLE OR NO WATER

FIELD OF THE INVENTION

This application is a 371 of PCT/EP/02620 filed Sep. 27, 1993. The invention relates to a method for the preparation of tert.-alkyl hydroperoxides of little or no water content in inert organic solvents by dehydration with $H_2SO_4$.

BACKGROUND OF THE INVENTION

Due to the way they are made, alkyl hydroperoxides are available only with a relatively high water content. Also, water is added as an especially cheap and suitable phlegmatizing agent for transportation and in storage, in order thus to assure safe handling of these hydroperoxide reagents which have a tendency to explosive degradation. For example, the technically very important tert.-butyl hydroperoxide (TBHP) is approved for transportation only as TBHP-70 (70% TBHP and 30% water) and as TBHP-80 (80% TBHP, approximately 8% di-tert.-butyl peroxide and 12% water). Although the water content of such reagents has no undesirable effect in a number of applications, as initiators in emulsion polymerization for example, it has been found, however, that any appreciable water content is undesirable in other organic syntheses, as for example in the case of asymmetrical epoxidation, and even prevents it in many cases. For a long time, therefore, efforts have been made to prepare concentrated, water-free solutions of alkyl hydroperoxides.

For example, P. D. Bartlett et al, in J. Am. Chem. Soc. 80, 1398 (1958), has proposed a method, which was later improved by Böck, Dissertation Univ. of Munich, 1968, to remove water from tert.-butyl hydroperoxide (TBHP) by means of an azeotropic vacuum distillation. In this process TBHP has to be warmed to about 50° to 70° C., which entails a high risk of explosion. Therefore this procedure is not appropriate for application on a technical scale.

In J. Org. Chem. 1983, 48, 3607–3608, J. G. Hill et all describe the use of benzene and toluene for the azeotropic removal of water: benzene or toluene is added to the aqueous TBHP solution and the water is distilled out with refluxing until a constant well temperature indicates the complete removal of the water. This process, however, likewise has the disadvantage that the temperature has to be raised to quite considerable temperatures, namely to as much as 107° C. Consequently this method too is unsuitable for the industrial scale on account of thermal stress in a sealed distillation apparatus due to the problems that threaten safety. Moreover, the concentrations obtained by this method are too low.

H. Langhals et al., Chem. Ber. 113, 3662–3665 (1980), describes the use of molecular sieves for drying TBHP and expressly states that acid drying agents, such as concentrated sulfuric acid or phosphorus pentoxide are not suitable for removing water from TBHP containing water, since they are said to lead to the degradation of the peroxides. The process proposed by Langhals et al. for repeated drying with molecular sieves is very costly in time and material and therefore it is not suitable for production on a technical scale. Moreover, the molecular sieve used must be free of heavy metals and has to be given complicated treatment before use. Just for drying, the TBHP must, according to the; example given, be treated five times at –4° C. for 3 hours to achieve sufficient water removal.

The invention therefore has the purpose of developing a simple drying process for tertiary alkyl hydroperoxides which can be performed on a technical scale with easily handled commercial chemicals.

OBJECT OF THE INVENTION

DESCRIPTION OF THE INVENTION

This purpose is achieved in accordance with the invention by a method for the preparation of solutions of alkyl hydroperoxides of little or no water content in inert solvents by dewatering with $H_2SO_4$, which is characterized in that one or more inert organic solvents as well as sulfuric acid are added in such amount and concentration to an aqueous solution of the tert.-alkyl hydroperoxide that at least 49% $H_2SO_4$ is present in the aqueous phase that develops after mixing and then separating the phases, and the water content in the organic phase amounts to no more than 2.5%. In this manner a satisfactory dewatering of the alkyl hydroperoxide solutions can be accomplished.

Preferably the method of the invention is practiced in such a manner that in a first dewatering step, by adding one or more inert organic solvents and a small mount of sulfuric acid to an aqueous solution of the tert.-alkyl hydroperoxide, a mixture consisting of an aqueous and an organic phase is formed; after separation of the phases the organic phase is separated from the aqueous phase in a manner known in itself, and in at least one additional dewatering step, as much $H_2SO_4$ is added to the organic phase as is necessary to reduce the water content in the organic phase to no more than 2.5%, the amount of acid being selected such that, in the final dewatering step, at least 49% $H_2SO_4$ is in the aqueous phase, and if desired still another amount of the organic solvent or solvents is added, and again the aqueous phase is separated in a manner known in itself.

For it was found surprisingly that alkyl hydroperoxides can be dewatered especially advantageously with more or less concentrated sulfuric acid without significant degradation if an aqueous alkyl hydroperoxide solution is mixed with an inert organic solvent and at first only a small amount of the sulfuric acid needed for the removal of water is added. At least as much $H_2SO_4$ is added that an aqueous phase and an organic phase forms. After separation of the aqueous phase, in at least one additional dewatering step, as much $H_2SO_4$ is added as is needed in order to separate the water from the aqueous phase to the desired degree, namely no more than 2.5 residual water, if measured by the method of Karl Fischer (Angew. Chemie 47 (1935), 394). The aqueous phase thus obtained is again separated in a manner known in itself. The required total amount of sulfuric acid can be determined easily by simple measures known to the expert or can quickly be determined by simple experiment. In the final step the sulfuric acid concentration should amount to at least 49%, and higher levels, up to about 53%, are also advantageous. What concentrations may be desirable must be checked in connection with the possible safety risks.

The method of the invention is especially suitable for low, especially tertiary $C_4$–$C_6$ alkyl hydroperoxides, tert.-butyl hydroperoxide and tert.-amyl hydroperoxide being especially preferred.

In the method of the invention, an $H_2SO_4$ of at least 50%, and preferably one of about 72% $H_2SO_4$. A commercial concentrated sulfuric acid or even oleum can be used in the method of the invention, although for reasons of effectiveness on the one hand, and for reasons of safety on the other, the approximately 72% $H_2SO_4$ has proven to be especially suitable.

In the method of the invention it has also proven expedient to add 0.05 to 15 g of $H_2SO_4$, and preferably 0.5 to 5 g of $H_2SO_4$ per 100 g of water. It is especially preferred to add 0.1 to 10 g of sulfuric acid per 100 g of the water present in the mixture of the first dewatering step.

In the further dewatering step it has proven advantageous to add 5–100 g $H_2SO_4$ per 100 g of originally present $H_2O$. Especially desirable is 35–75 g, but 40–60 g is very especially preferred.

In an especially preferred embodiment of the invention, three dewatering steps are performed, and in the third step another 5–30 g $H_2SO_4$ and preferably 8–20 g $H_2SO_4$ are used per 100 g of the originally present water, in order to reduce still further the water content of the alkyl hydroperoxide solution. It is very especially preferred to use in the third dewatering step 10–15 g $H_2SO_4$ per 100 g of the water originally present.

If in the method of the invention a sulfuric acid is used which has a concentration of less than 100%, the water content of this sulfuric acid must be figured in with the amount of the water originally present.

If still more intensive drying is desired than is possible with $H_2SO_4$, it has proven desirable to remove the minimal residual water content by means of molecular sieves, and thus to obtain a virtually completely dewatered or dry tert.-alkyl hydroperoxide solution. It has also been found desirable to remove any sulfuric acid still adhering to the solutions dewatered according to the invention by means of neutralization. The neutralization is usually performed with a solid base. The solid base is then separated from the neutralized solution by means of methods known in themselves. Expedient methods are filtration, decantation and centrifugation of the solution. Especially suitable bases are carbonates and bicarbonates, the alkali and alkaline earth salts being especially suitable. Sodium carbonates and potassium carbonates and bicarbonates have proven especially suitable, the sodium salts being again preferred.

In the method of the invention, any solvents can be used which are phlegmatic and/or inert to the tert.-alky hydroperoxides and to any possible substances reacting therewith. Therefore, aliphatic, cycloaliphatic and aromatic hydrocarbons, and especially their halogen derivatives, are suitable for the method of the invention. Those solvents have proven especially suitable for the method of the invention which have a boiling point above 150° C. Isododecane is used in the method of the invention as a very especially preferred phlegmatizing solvent. On account of the reactivity of the hydroperoxides it has proven to be expedient in practice to adjust the concentration of the hydroperoxides such that the tert.-alkyl hydroperoxide content in the inert solvent does not exceed 75%, and preferably 65%. In general, so much solvent is added that the solutions have a content of 20–75% and 40–65% peroxide, respectively. Higher contents, however, are by no means excluded.

In the method of the invention it has also proven expedient in the first dewatering step to add only a part of the solvent, namely up to 80% at most, usually 20–80%, and preferably 30–50%. The remaining solvent is then added either in portions or even all at once in the next dewatering steps. The addition of the remainder of the solvent in the second dewatering step has proven especially expedient.

In the method of the invention it has proven advantageous to extract with the inert solvent the separated aqueous sulfuric acid solution after it has been separated. This inert solvent can then be used in the dewatering method of the invention, thereby increasing the yield. It is also expedient in the method of the invention to reuse the sulfuric acid solution for new water mixtures. It is possible in that case to use the sulfuric acid obtained in later dewatering steps for the removal of water in the first dewatering step. It is also possible, however, to adjust the aqueous sulfuric acid to the concentration needed in the same or any other dewatering step by adding concentrated $H_2SO_4$ or oleum.

The method of the invention permits the virtually complete dewatering of tert.-alkyl hydroperoxides, requires no input of energy for its practice, and can be performed by means of ordinary, simple and undemanding equipment. Furthermore, only small amounts of common commercial chemicals are needed, which also are recyclable into the process for the production of the corresponding hydroperoxides (alcohol +$H_2O_2$/$H_2SO_4$).

The following examples are intended to further explain the invention.

EXAMPLE 80 g of isododecane and 2 ml of a 72% $H_2SO_4$ solution are added to 900 g of TBHP-70 (with a water content of 270 g $H_2O$), and after establishing equalization of the phases, the concentration of water, $H_2SO_4$ and hydroperoxide was determined in each phase. The results are given in the following table.

In a second dewatering step after separating the aqueous phase, then another 200 g of isododecane and 105 ml of the 72% $H_2SO_4$ was added, and after phase equilibrium was established, the concentration in each phase was determined as described above. After separation of the aqueous phase another 30 ml of 72% $H_2SO_4$ was added and the content of the reactants in each phase was determined as before. The results are also shown in the table that follows.

After neutralization with 12 g of solid sodium carbonate and filtration, 860 g of solution was obtained with a TBHP content of 67%, which corresponds to a yield of 91% of the amount put in.

The determination of the water content in the organic phase was performed by the method of Karl Fischer (Karl Fischer reagent supplied by Riedel de Haän).

|  | Extraction Step | | |
| --- | --- | --- | --- |
|  | 1 | 2 | 3 |
| Put in: | | | |
| TBHP-70 | 900 g | | |
| Isododecane | 80 g | 200 g | |
| $H_2SO_4$, 72% | 2 ml | 105 ml | 30 ml |
| Organic phase | | | |
| Water, %* | 19.0 | 3.5 | 1.7 |
| $H_2SO_4$, % | 0.05 | 0.1 | 0.25 |
| TBHP, % x) | 70–72 | 64–66 | 65–67 |
| Aqueous phase | | | |
| TBHP, % | 14.8 | 3.6 | 4.0 |
| $H_2SO_4$, % | 1.6 | 39.0 | 52.0 | x) Limits from various experiments
*In using the Karl-Fischer reagent for the determination, values of about 0.6% water were obtained even with the aid of solutions dewatered completely with molecular sieves. This bottom figure is conditioned by the method, and therefore the water content data is actually about 0.6% lower than stated.

After neutralization with 12 g of solid sodium carbonate, and filtration, about 860 g of solution is obtained, with a TBHP content of 66–67%, corresponding to 91% of the amount put in.

We claim:

1. Method for the preparation of solutions of tert.-alkyl hydroperoxides in inert solvents with little or no water content by dewatering with $H_2SO_4$, which comprises adding to an aqueous solution of the tert.-alkyl hydroperoxide, one or more inert organic solvents as well as sulfuric acid in an amount and concentration such that, in the aqueous phase forming after the mixing and subsequent separation of the phases, there is at least 49% of $H_2SO_4$ and the water content in the organic phase amounts to no more than 2.5%.

2. Method according to claim 1, wherein in a first dewatering step, by the addition of one or more inert organic solvents and a small amount of sulfuric acid to an aqueous solution of the tert.-alkyl hydroperoxide a mixture consisting of an aqueous and an organic phase forms, after separation of the phases the organic phase is separated from the aqueous phase in a manner known in itself, and to the organic phase, in at least one additional dewatering step, as much $H_2SO_4$ is added as is needed to reduce the water content in the organic phase to 2.5% at most, the acid amount being selected such that in the final dewatering step at least 49% $H_2SO_4$ is in the aqueous phase, if necessary still another amount of the organic solvent or solvents is added, and again the aqueous phase is separated in a manner known in itself.

3. Method according to claim 1 wherein an at least 15%, and especially an at least 50% sulfuric acid is used.

4. Method according to claim 1, wherein a 72% sulfuric acid is used.

5. Method according to claim 1, wherein the alkyl hydroperoxide solution of little or no water content is neutralized with a solid base.

6. Method according to claim 5, wherein neutralization is performed with a carbonate and/or bicarbonate.

7. Method according to claim 6, wherein the carbonate or bicarbonate is an alkali salt and/or alkaline earth salt.

8. Method according to claim 7, wherein the alkali salt is a potassium and/or sodium salt.

9. Method according to claim 2, wherein in the first dewatering step 0.05 to 15 g of $H_2SO_4$ is added per 100 g of water.

10. Method according to claim 2, wherein in the first dewatering step 0.5–5 g of $H_2SO_4$ is added per 100 g of water.

11. Method according to claim 2, wherein in at least one additional dewatering step, 5 to 110 g of $H_2SO_4$ is added per 100 g of the $H_2O$ originally present.

12. Method according to claim 2, wherein in at least one additional dewatering step, 35–75 g of $H_2SO_4$ is added per 100 g of the $H_2O$ originally present.

13. Method according to claim 2, wherein three dewatering steps are performed, and in the third dewatering step with 5–30 g $H_2SO_4$ per 100 g of the water originally present the water content is still further reduced.

14. Method according to claim 13, wherein in the third dewatering step 8–20 g of $H_2SO_4$ is used per 100 g of the water originally present.

15. Method according to claim 1, wherein the already dewatered alkyl hydroperoxide is further dried with a molecular sieve.

16. Method according to claim 1, wherein the inert, organic solvent is an aliphatic, cycloaliphatic or aromatic hydrocarbon or a mixture thereof.

17. Method according to claim 16, wherein the solvent has a boiling point that is greater than 150° C.

18. Method according to claim 16, wherein the solvent is isododecane.

19. Method according to claim 16, wherein the solvent is a halogenated solvent.

20. Method according to claim 1, wherein the t-alkyl hydroperoxide is a $C_4$ to $C_6$ alkyl hydroperoxide.

21. Method according to claim 2, wherein in the first step no more than 50% of the inert solvent is added.

22. Method according to claim 2, wherein in the first step no more than 30% of the inert solvent is added.

23. Method according to claim 2, wherein the separated aqueous phases are extracted with the inert solvent and the latter is used for additional alkyl hydroperoxides to be dewatered.

* * * * *